United States Patent [19]

Rottermann

[11] Patent Number: 4,991,243
[45] Date of Patent: Feb. 12, 1991

[54] RADIATION-PERMEABLE BODY SUPPORT

[75] Inventor: Robert Rottermann, Waedenswil, Switzerland

[73] Assignee: Rottermann AG, Switzerland

[21] Appl. No.: 221,259

[22] PCT Filed: Aug. 17, 1987

[86] PCT No.: PCT/CH87/00101

§ 371 Date: Aug. 23, 1988

§ 102(e) Date: Aug. 23, 1988

[87] PCT Pub. No.: WO88/03004

PCT Pub. Date: May 5, 1988

[30] Foreign Application Priority Data

Oct. 29, 1986 [CH] Switzerland ............ 4283/86-6

[51] Int. Cl.$^5$ ............ A61G 7/05; H05G 1/00
[52] U.S. Cl. ............ 5/60; 5/190; 378/209
[58] Field of Search ........ 5/190, 212, 60, 70, 5/66, 62; 378/68, 209, 208; 297/452

[56] References Cited

U.S. PATENT DOCUMENTS

| 198,892 | 1/1878 | Magers | 5/190 |
|---|---|---|---|
| 532,850 | 1/1895 | Wangersheim | 5/70 |
| 1,263,611 | 4/1918 | Scroggin | 5/60 |
| 1,389,480 | 8/1921 | Berman | 5/60 |
| 1,529,490 | 3/1925 | Lolmaugh | 5/70 |
| 2,636,793 | 4/1953 | Meyer | 378/209 |
| 2,667,169 | 1/1954 | Kambourakis | 5/60 |
| 3,373,454 | 3/1968 | Curtis | 5/66 |
| 3,609,357 | 9/1971 | Jones | 378/209 |
| 3,814,414 | 6/1974 | Chapa | 5/60 |
| 3,868,103 | 2/1975 | Pageot | 5/66 |
| 4,395,786 | 8/1983 | Casey | 5/66 |
| 4,456,301 | 6/1984 | Apissomian | 297/452 |
| 4,589,126 | 5/1986 | Augustsson | 378/209 |
| 4,750,784 | 6/1988 | Schwartz | 297/452 |

FOREIGN PATENT DOCUMENTS 77436 3/1960 France .................. 5/70

OTHER PUBLICATIONS

Leaflet, "Varian", published in 1982.

Primary Examiner—Gary L. Smith
Assistant Examiner—F. Saether
Attorney, Agent, or Firm—Tarolli, Sundheim & Covell

[57] ABSTRACT

The body support can be used as a part of the reclining surface in a patient's couch intended for use in radiation therapy. It consists of a H-shaped frame with two parallel lateral beams linked together by a central transverse beam. The supporting surfaces divided by the central transverse beam are provided with transparent string tensioning which is secured exclusively to the two lateral beams. The external edges of the body support parallel to the central beam are free of radiation-attenuating frame elements so that uninterrupted dynamic radiation treatment is possible when the direction of radiation is changed from one side of the supporting surface to the other one.

5 Claims, 1 Drawing Sheet

RADIATION-PERMEABLE BODY SUPPORT

BACKGROUND OF THE INVENTION

The present invention refers to a radiation-permeable body support usuable as a part of the reclining surface in a patient's couch intended for use in radiation therapy. It consists of a frame having a transparent stringing whereby a central transverse beam of the frame is provided which divides the support into two supporting surfaces.

This body support is used instead of a portion of the normal reclining surface if the part of the body of a patient has to be treated by radiation directly as well as from the bottom side of the reclining surface during a single treatment cycle. For this purpose, usually a radiation source. e.g. an X-ray emitting apparatus is used which is displaceable in a vertical plane along a circular path.

The supporting surfaces have to be transparent in order to enable the treatment ray to be aligned to a treatment area optically outlined on the body portion and made visible by means of a pilot light in order to put the operator into a position to correct the alignment of the treatment ray if the patient changes its position unpredictably

PRIOR ART

A known body support of the kind mentioned herebefore comprises a rectangular frame with a central transverse beam dividing the reclining surface into two support surfaces. The frame is provided in each support surface with a stringing consisting of crossed strings anchored on parallely running frame parts. The frame must be rigidly constructed in order to withstand the stringing forces. Thus, the parts of the frame must have such a size that the radiation is unduly attenuated. In order to avoid this disadvantage, the frame is laterally displaceably mounted in a gate shift means. This makes possible that the central transverse beam as well as the outer frame parts running parallel thereto can be together positioned such that they are situated beyond the reach of the treatment rays during a static radiation therapy. However, particularly troublesome is the attenuating effect of the said outer frame parts during a dynamic radiation therapy because the radiation treatment is interrupted upon the transition of the direction of the radiation from one side of the support surface to the other one.

SUMMARY OF THE INVENTION

In order to avoid this disadvantage, the present invention provides a radiation-permeable body support having a H-shaped frame whereby at least one of the support surfaces is provided with a stringing which is secured exclusively to the two lateral beams running parallel to each other and being interconnected by the central transverse beam. Thus, any frame parts which could attenuate the radiation are omitted and no means are required for laterally shifting the frame.

Preferably, the lateral beams of the H-shaped frame are biased such that they run parallel with regard to each other under the influence of the stringing.

According to a preferred embodiment, at least one string consisting of radiation-resistive material, e.g. made of plastic material, is provided for the stringing of the support surface, forming the support surface in parallely running portions having identical distance and having a meander-like disposition. The stringing can be reinforced at the end portions of the beams, e.g. by providing a further string running from one beam to the opposite one in several windings.

In order to ensure an improved distribution of the pressure in the region of the support surface occupied by the body of the person resting on the body support and in order to avoid that the string portions laterally evade upon a load exerted in a small area, the stringing can be provided with a transparent radiation-resistant covering foil which is secured to the two lateral beams of the frame as well.

Instead of using strings for the stringing of the body support, another possibility consists in using a transparent support foil consisting of one part or a plurality of parts which can be reinforced by additional strings at the outer edges interconnecting the two lateral beams.

BRIEF DESCRIPTION OF THE DRAWINGS

In the following, the invention will be further described with reference to an embodiment shown in the drawing. In the drawing

DESCRIPTION OF A PREFERRED EMBODIMENT

Figure 1:
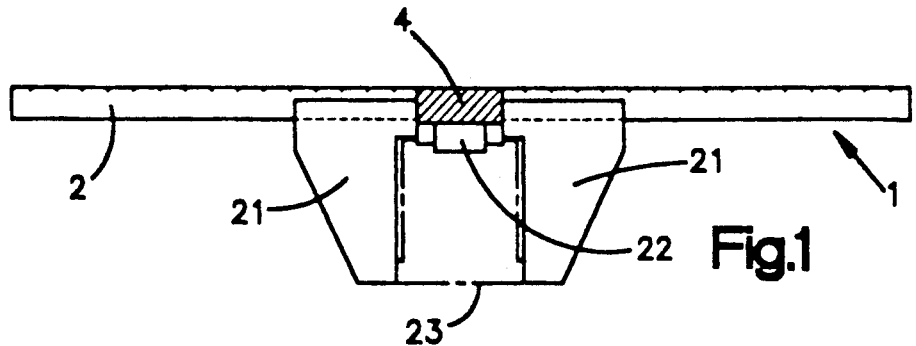
FIG. 1 shows a cross section of the body support.

The radiation-permeable body support shown in the drawing comprises a H-shaped frame 1 consisting of two parallel lateral beams 2 and 3 and a central transverse beam 4 interconnecting the two lateral beams 2 and 3. Preferably, the beams 2, 3 and 4 are made of metal, e.g. a tough, hard aluminium alloy, or of a fiber-reinforced plastic material.

The frame 1 is provided with a transparent stringing which is divided into two support surfaces 5 and 6 by the central transverse beam 4; both support surface 5 and 6 together form the reclining surface. To form the stringing of the two support surfaces 5 and 6, there is provided, in each case, a string 7 and 8, respectively, made of radiation-resistant plastic material and forming the support surfaces in parallely running portions having identical distance and having a meader-like disposition. The ends of the strings 7 and 8 provided with knots 9 and 10 and the U-turn portions 11 of the strings are secured to the lateral beams 2 and 3 of the frame 1. The U-turn portions 11 are embedded in semicircular grooves within the lateral beams. Instead of one single string, two or more strings can run parallel to each other. All portions of the strings 7 and 8 are tensioned to such a high degree, e.g. with 500N in the case of a portion length of 50 cm, that the sagging of the strings does not exceed a few millimeters if the support surfaces are loaded with the body portion of a person resting thereon. The lateral beams 2 and 3 are biased in order to compensate for the load exerted by the stringing. The ends of the lateral beams 2 and 3 are provided with a further string portion 12 and 13, respectively, in order to reinforce the stringing; the strings 12 and 13 are tensioned and run from one beam to the other beam 2 and 3, repectively, in several overlaying windings.

Figure 3:
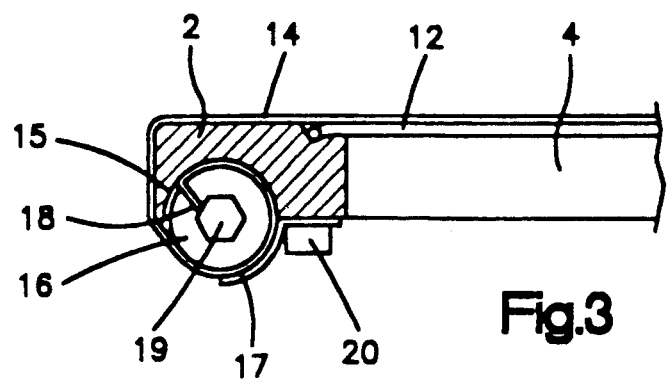
FIG. 3 shows a detailed view of the tensioning means for a covering foil in a larger scale.

The entire support surface is overlaid with a tensioned covering foil 14 which is likewise anchored to the two lateral beams 2 and 3 of the frame 1. Details of the tensioning device serving for tensioning the covering foil 14 are shown in FIG. 3. The lateral beams 2 and 3 comprise each a longitudinal groove 15 located at their lower side. The grooves 15 are semi-cylindrical in cross section. A tension roller 16 is mounted in each of these grooves 15, located on both sides of the central beam 4 and held in position by means of a clamping strap 17. Each tension roller has, on its periphery, a longitudinal slot 18 into which is inserted an edge portion of the covering foil 14 looping around the tension rollers 16. In order to rotate the tension rollers when the clamping straps 17 are released and, thus, in order to generate a tensioning force, each tension roller 16 is provided on its end faces with a hexagonal opening 19 serving to insert an angled hexagonal wrench. When the covering foil 14 is in its tensioned state, the tension roller 16, together with the associated edge portion of the covering foil, can be fixed to the beam in the longitudinal groove 15 pressing down the clamping strap 15 by means of screws which are arranged along the latter and of which one is shown and designated by reference numeral 20.

A one-part or multi-part transparent support foil can be provided for the covering instead of strings. For tensioning the support sheet, basically the same means can be provided as was described hereinbefore for tensioning the covering foil.

The base part of a treatment couch intened for use in radiation therapy normally has a cantilevered beam over which the support surface of the couch extends. The body support as hereinbefore described is intended to be placed on this cantilevered beam where it forms part of the couch top. For this purpose, the frame 1 is provided on the two ends of its central beam 4 with guide jaws 21 and guide bolt 22 cooperating with corresponding guide surfaces on the cantilevered beam 23 indicated by broken lines in FIG. 1; thus an accurate positioning of the body support is made possible.

Figure 2:
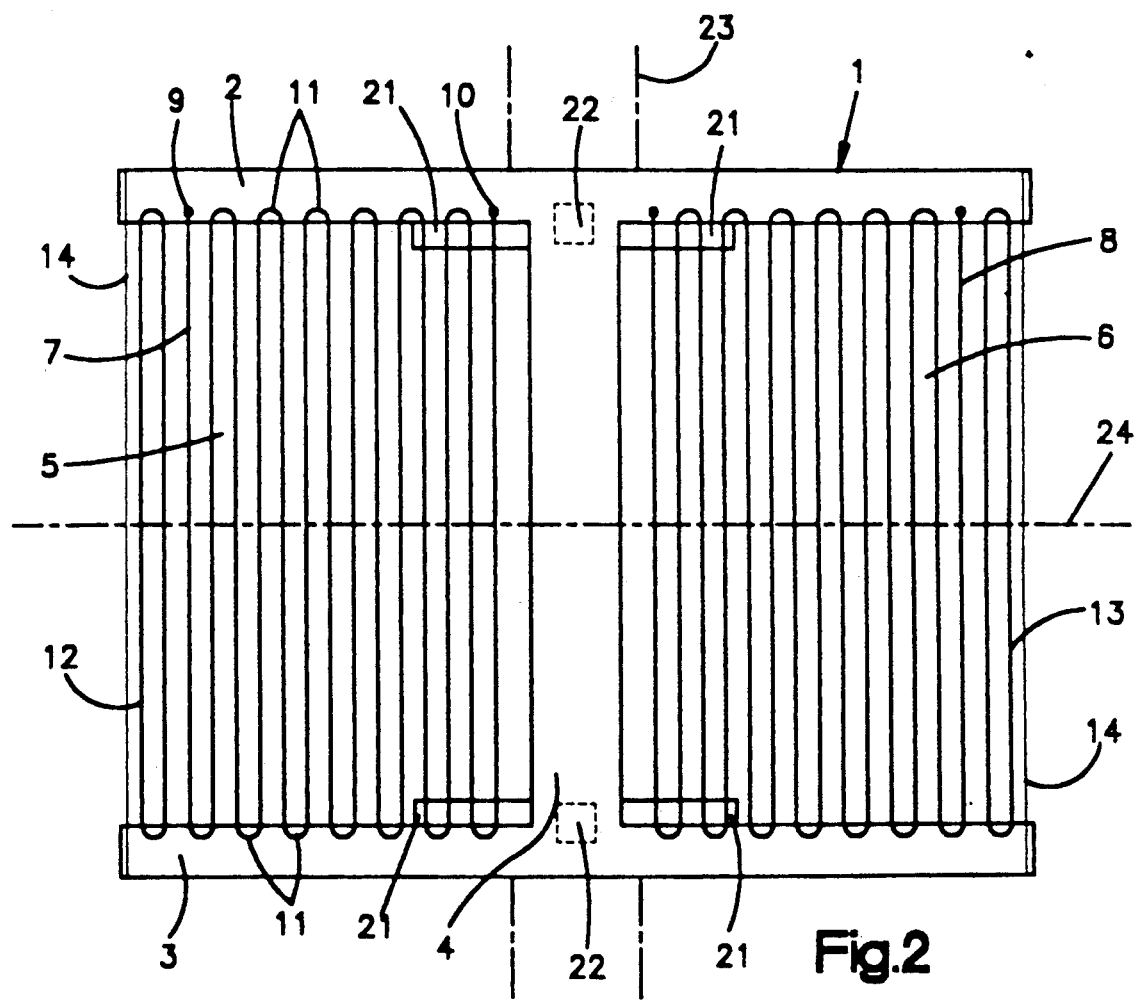
FIG. 2 shows a top view of the body support.

In fig. 2, the broken line 4 indicates the track of the vertical plane in which the circular path of the radiation emitting apparatus runs.

Under certain circumstances, it may be expedient to provide the frame with a radiation-permeable string for forming on one of the two supporting surfaces only and to design the other supporting surface in the form of a radiation-opaque plate.

What I claim is:

1. A radiation-permeable body support having a body support surface as a part of the reclining surface in a patient's couch used in radiation therapy in which a radiation emitting apparatus moves in a first plane, comprising:
   an H-shaped frame having two parallel lateral beams and a central beam interconnected between said two parallel lateral beams, said central beam extending transverse to the first plane and dividing the body support surface into two supporting surfaces lying in a second plane transverse to the first plane, said two parallel beams being in the same plane as said central beam and not connected by any frame parts other than said central beam; and
   a transparent stringing being anchored solely to said two parallel lateral beams connected to one another by said central beam and forming at least one of said two supporting surfaces.

2. A body support according to claim 1, in which said lateral beams are outwardly biased.

3. A body support according to claim 1, in which at least one string is provided for the stringing forming said one supporting surface, said stringing being arranged in a meander-like disposition in parallel portions at uniform distances from one another.

4. A body support according to claim 3, in which said stringing is reinforced at the ends of said lateral beams.

5. A body support according to calim 3, in which said stringing is covered with a transparent covering foil which is likewise braced between said two parallel lateral beams of said frame.

* * * * *

UNITED STATES PATENT AND TRADEMARK OFFICE
CERTIFICATE OF CORRECTION

PATENT NO. : 4,991,243

DATED : February 12, 1991

INVENTOR(S) : Robert Rottermann

It is certified that error appears in the above-identified patent and that said Letters Patent is hereby corrected as shown below:

Column 4, Line 37, Claim 5, change "calim" to --claim--.

Signed and Sealed this

Tenth Day of November, 1992

Attest:

DOUGLAS B. COMER

*Attesting Officer*    *Acting Commissioner of Patents and Trademarks*